(12) United States Patent
Bruzzese et al.

(10) Patent No.: US 6,586,407 B1
(45) Date of Patent: Jul. 1, 2003

(54) INJECTABLE PHARMACEUTICAL FORMULATIONS FOR PARTRICIN DERIVATIVES

(75) Inventors: Tiberio Bruzzese, Milan (IT); Valerio Maria Ferrari, Mc Monaco (MC)

(73) Assignee: Quatex N.V., Curacao (AN)

( * ) Notice: Subject to any disclaimer, the term of this patent is extended or adjusted under 35 U.S.C. 154(b) by 0 days.

(21) Appl. No.: 09/720,236

(22) PCT Filed: Mar. 11, 1999

(86) PCT No.: PCT/EP99/01571

§ 371 (c)(1),
(2), (4) Date: Dec. 22, 2000

(87) PCT Pub. No.: WO99/66902

PCT Pub. Date: Dec. 29, 1999

(30) Foreign Application Priority Data

Jun. 25, 1998 (IT) .......................................... MI98A1457

(51) Int. Cl.⁷ ............................................... A61K 31/70
(52) U.S. Cl. ......................... 514/31; 514/514; 514/450; 544/106
(58) Field of Search .......................... 544/106; 514/450, 514/31

(56) References Cited

U.S. PATENT DOCUMENTS

| 3,780,173 A | * | 12/1973 | Bruzzese et al. | ............ 424/122 |
| 3,961,047 A | * | 6/1976 | Bruzzese et al. | ............ 424/122 |
| 4,017,603 A | * | 4/1977 | Ferrari et al. | ................ 424/122 |
| 5,298,495 A | * | 3/1994 | Bruzzese et al. | ............. 514/31 |

FOREIGN PATENT DOCUMENTS

WO    WO 9802168 A1  *  1/1998  .......... A61K/31/70

OTHER PUBLICATIONS

Osol, A. Editor–in–Chief, Remington's Pharmaceutical Sciences, 15TH Edition, 1975, pp. 1241 and 1242.*

* cited by examiner

Primary Examiner—Dwayne C. Jones
(74) Attorney, Agent, or Firm—Oblon, Spivak, McClelland, Maier & Neustadt, P.C.

(57) ABSTRACT

New injectable pharmaceutical formulations are described, containing a partricin derivative in the form of a free base as the active ingredient, or a pharmaceutically acceptable water-soluble salt thereof in a solubilizing/dispersing medium made up of a lipid and/or phospholipid emulsion in water, a procedure to obtain them, and the use of the formulations in the treatment of phathologies sensitive to the action of partricin derivatives.

43 Claims, No Drawings

INJECTABLE PHARMACEUTICAL FORMULATIONS FOR PARTRICIN DERIVATIVES

This application is a 371 of PCT/EP99/01571, filed on Mar. 11, 1994.

This invention relates to new injectable pharmaceutical formulations containing partricin derivatives as the active ingredient. In particular, the new pharmaceutical formulations enclose at least one derivative of partricin in the form of a free base, or a pharmaceutically acceptable water-soluble salt of it, in a solubilizing/dispersing medium made up of a lipid and/or phospholipid emulsion in water.

In patent applications EP-A-0434943 (equivalent to U.S. Pat. No. 5,296,597) and EP-A-0489308 (equivalent to U.S. Pat. No. 5,298,495) several derivatives of partricin A and/or B (henceforth "partricin") are described, wherein the carboxyl in position C-18 of the macrolidic ring is in the form of an ester or of a neutral amide or of an amide containing a basic nitrogen group in the side chain and where the primary amino group of mycosamine can optionally form an amide bond with the carboxyl of an acid, it too containing a basic nitrogen group in the chain.

The afore-said documents also describe the preparation of their salts with acids, acceptable from a pharmacological and pharmaceutical point of view, and report that such salts are unusually water-soluble.

It has already been ascertained that the partricin derivatives, described in the afore-said European patent applications, can also be used in clinical practice, for human and veterinary application as drugs for treatment of several pathologies sensitive to the partricin derivatives; in particular, injectable formulations may be prepared enclosing such derivatives, evidencing the advantages deriving from the water-solubility of the said partricin derivatives. These formulations may permit, for instance, using a derivative of partricin's as the active ingredient (e.g., N-dimethylaminoacetyl-partricin A 2-dimethylamino-ethylamide diascorbate—code name SPA-S-843) for instance with the addition of ascorbic acid, as antioxidant, and of lactose as excipient. The freeze-dried product is normally dissolved in 5% glucose solution at the time of use and administered by slow intravenous infusion.

Even though this formulation can be of concrete utility in the clinical practice, it was however found that such aqueous formulations of partricin derivatives, specially when repeatedly administered and with daily frequency, can cause local vascular damage with considerable pain at the site of injection, tissue irritation, edema formation and thickening of vasal epithelium, leading in the end, to massive formation of thrombi and onset of frank thrombophlebitic forms.

It has now been surprisingly found that these side effects involving the vascular system, brought about by intravenous injections of known formulations of the partricin derivatives, can be considerably limited, or even avoided, by the use of new formulations wherein the partricin derivative is enclosed in a lipid and/or phospholipid emulsion in water.

One of the subjects of the present invention is in fact an injectable pharmaceutical formulation enclosing at least one partricin derivative in the form of free base—or of water-soluble pharmaceutically acceptable salt thereof, with acids that are acceptable from a pharmaceutical and pharmacological point of view—in a solubilizing/dispersing medium made up of a lipid and/or phospholipid emulsion in water such that the resulting emulsion be iso-osmotic.

In the present invention the expression "partricin derivative" indicates the derivatives of partricin described in patent applications EP-A-0434943, EP-A-0489308, GB-A-1359473 (equivalent to U.S. Pat. No. 3,780,173) and GB-A-1046774 (equivalent to U.S. Pat. No. 3,961,047). In particular, preferred formulations are those wherein the partricin derivative is a derivative of partricin A and/or B presenting the carboxyl in position C18 of the macrolidic ring in the form of ester or of neutral amide or of amide containing a basic nitrogen group in the side chain, and those wherein the derivative is further substituted, on the primary amino group of mycosamine in the form of amide with an acid containing a basic nitrogen group in the side chain. A partricin derivative specially preferred for the formulations of the invention is N-dimethylaminoacetyl-partricin A 2-dimethylamino-ethylamide. When the formulations of the invention enclose a partricin derivative in the form of a free base, the addition of a surfactant and/or a co-solvent is preferred in order to avoid any eventual problem of active ingredient solubilization before its inclusion in the lipid emulsion; alternatively, this trouble can be avoided by sonication of the particles, elevation of the system temperature e.g., from room temperature to 40–50° C., and etc.

In the case the formulations of the invention enclosed a pharmaceutically acceptable salt of the partricin derivative, these salts are preferably formed with at least one, preferably two, acid equivalents, preferably ascorbic or aspartic acid; the salt preferred for the formulations of the invention is N-dimethylaminoacetyl-partricin A 2-dimethylamino-ethylamide diascorbate, as such or as its free base.

The formulations of the invention comprise a pharmaceutically effective quantity of the partricin derivative; the dose of partricin derivative per unit to be administered remains substantially equal to that of the traditional formulations. In particular, the quantity ranges from 1 to 100 mg, preferably 10 to 50 mg.

The partricin derivative enclosed in the formulations of the invention is, preferably, in the form of solution, of micellar pseudosolution, of encapsulated inclusion compound, or of suspension of sub-micronized particles, their size being smaller than 5 $\mu$m. preferably smaller or equal to 3 $\mu$m, to avert the risk of pulmonary embolism; following sterilization (by sterilizing filtration or other suitable method), the partricin derivative can directly be added to the lipid emulsion or, preferably, stored in the dry state, following suitable processing (e.g., through freeze-drying), to improve long-term stability and be added to the lipid emulsion just prior to its therapeutic use by parenteral injection, particularly intravasal and, preferably, intravenous route.

In the formulation of the invention, the solubilizing/dispersing medium, is a lipid emulsion, preferably oil-in-water, containing lipids and/or phospholipids, in the form of droplets, vesicles, nanospheres, etc.

The lipids and/or phospholipids used in the formulations of the present invention can be from different origin, that is, animal and/or vegetable and/or synthetic and/or semisynthetic origin (hydrogenated fats and the like).

The lipids are preferably taken from the group of the mono-, di- or triglycerides; specially triglycerides; when of vegetable origin preferably from olives, for instance triolein, or from soybeans, when of animal origin preferably fish oils.

The phospholipids, in particular the phosphatidylcholines, when of vegetable origin are typically soybean lecithins, when of animal origin are selected preferably from egg yolk lecithins.

Other phospholipids, preferred for the formulations of the invention, are those selected from the group of the distearoilphosphatidyl-choline, dimyristoilphosphatidylcholine, dimyristoilphosphatidylglycerol, phosphatidyl-ethanolamine, phosphatidylserine, phosphatidyl-inositol.

Hydrogenate lipids and/or phospholipids too can be used in the formulations of the invention.

When phospholipids are used alone, they can be in the form of multilamellar or unilamellar, large or small vesicles, optionally containing sterols. In other cases, lipids and/or phospholipids can be present in the form of lipid nanospheres able to encapsulate the partricin derivative.

The concentration of the lipids eventually present in the formulations of the invention varies from 1 to 25%, being it usually 10–20% while the concentration of the phospholipids eventually present can vary from 0.05% to 5%.

The formulations of the invention can also enclose an excipient and/or a pharmaceutically acceptable adjuvant, such as those commonly used in the formulations intended for injectable use and according to the evidence of the experts in the field, for instance selected from the sugar group, preferably lactose, glucose, saccharose, maltose; antioxidants, preferably ascorbic acid, sodium ascorbate, vitamin E; preservatives, preferably alkyl paraben, benzyl alcohol; ionic or non-ionic surfactants, preferably sodium laurylsulfate, sodium deoxycholate, Tween®, particularly Tween 80, polysorbates, Cremophor (LE or other); acid or neutral or basic buffers, preferably mono- or bi-basic phosphates; co-solvents; stabilizers; polyalcohols such as i.e. glycerol, mannitol and xylitol; sterols such as cholesterol.

The formulations of the invention can moreover be realized in both a pharmaceutical form wherein the partricin derivative is already inserted in the lipid and/or phospholipid emulsion together with any eventual excipient and/or adjuvant, and in a pharmaceutical form wherein the partricin derivative is preserved in an anhydrous state (in the form, for instance, of a lyophile), together with any eventual excipient and/or adjuvant, separated from the lipid and/or phospholipid emulsion, together with any eventual excipient and/or adjuvant, in which it is extempore inserted before therapeutic administration.

The formulations of the invention are useful to prepare a medicament intended for the clinical treatment of pathologies sensitive to the action of the partricin derivative, such as, f.i., those described in EP-A-0434943, EP-A-0489308, GB-A-1359473 and GB-A-1046774 and several other pathologies. The texts of the four a/m documents are incorporated, for reference, in the present description, in particular as regards the partricin derivatives, their preparations and their described uses.

All the above mentioned products (lipids, phospholipids, excipients etc.) are commercially available and must be specially purified, fractioned and declared suitable for the injectable use (non pyrogenic etc.) The final composition should be such as to conduct to an iso-osmotic emulsion.

Industrial preparation of the emulsions requires the use of special equipment such as, in example, colloidal mills, two-stage pressure homogenizers, ultrasound generators, as is evident to an expert in the sector. Special attention will have to be paid to size control of the particles in suspension (sub-micron dimensions or, at any rate, not greater than 3–5 $\mu$m), to their distribution interval and their homogeneity, as well as stability of the emulsion itself, as is evident to an expert of the sector.

An additional item of the present invention consists in a procedure for preparation of the formulations of the invention, comprising sterilization—preferably by sterilizing filtration of the solution, micellar pseudo-solution, encapsulated compound or suspension of sub-micronized particles of the partricin derivative—and subsequent inclusion in the lipid and/or phospholipid emulsion.

Moreover, drying of the derivative is preferred—subsequent to sterilization and, at any rate, before inclusion in the lipid and/or phospholipid emulsion, of the solution, pseudo-solution or suspension of the partricin derivative—preferably through freeze-drying.

In the case that the partricin derivative be in the form of a free base, the procedure according to the invention can also comprise the addition of a surface active agent and/or a co-solvent to the partricin derivative or sonication of the particles or rising of the system temperature, passing, i.e., from room temperature to 40°–50° C., before inclusion of the derivative into the lipid and/or phospholipid emulsion. Incorporation of the drug in the lipid emulsion can occur in both the presence of the partricin derivative in the form of a solution, and in the solid state: in the latter case, the solid, for example a freeze-dried substance, can first be dissolved or dispersed in sterile water and the solution added to the emulsion or, better still, it can be directly solubilized with a portion of it. The final preparation will be sterile.

The final volume of the injectable formulation of the invention varies, in general from 5–10 ml when intended for bolus administration, to 100, 250, 500 ml when intended for slow, drip infusion over 1–5 hours, as evident to an expert of the sector.

As already mentioned, the formulations of the invention can unexpectedly reduce and even eliminate, the local irritating effects when used by intravascular route, contrary to what commonly occurs when using more traditional formulations as those obtained in glucose solution (5% glucose solution) or in physiological solution (0.9% sodium chloride solution). Moreover, the formulations of the invention allow, for instance, incorporation of the more lipophylic (hydrophobic) derivatives of partricin, in particular if in the form of free bases, in the inner oily phase of the oil-in-water emulsion, enabling the derivatives to be released over longer times and with particular tropism for the cells of the reticuloendothelial system and for the organs rich thereof, with relative decrease of the blood levels and wide changes of their toxicity. Viceversa, the more hydrophilic derivatives, along with their water soluble salts, specially when maintained in an acid pH medium, remain in the outer aqueous phase of the same oil-in-water emulsions, and retain their distribution in the body fluids substantially unchanged.

The following examples illustrate the invention without limiting it.

EXAMPLE 1

| Ampoule A - Active ingredient | |
|---|---|
| SPA-S-843 | 50 mg |
| Ascorbic acid | 4.5 mg |
| Lactose | 250 mg |
| Bidistilled water for injections (sterile, non pyrogenic) q.s. ad | 5 ml |
| Ampoule B - Diluent | |
| Soybean lipids | 1000 mg |
| Egg yolk phospholipids | 120 mg |
| Glycerol | 225 mg |
| Bidistilled water for injections | 10 ml |

The solution in ampoule A is freeze-dried and before use the solid residue re-dissolved with the diluent from ampoule B; the resulting mixture is slowly injected as a bolus dose, by intravenous route.

EXAMPLE 2

| | |
|---|---|
| Ampoule A - Active ingredient | |
| SPA-S-843 | 50 mg |
| Ascorbic acid | 4.5 mg |
| Lactose | 250 mg |
| Ampoule B - Diluent (see Example 1) | |

Before use the mixture of sterile powders in ampoule A is dissolved with the diluent from ampoule B and the mixture slowly injected as a bolus dose, by intravenous route.

EXAMPLE 3

| | |
|---|---|
| Ampoule A - Active ingredient (see Example 2) | |
| Vial B - Diluent | |
| Soybean lipids | 10 g |
| Egg yolk phospholipids | 1.2 g |
| Glycerol | 11.25 g |
| Bidistilled water for injections, q.s. ad | 100 ml |

The mixture of sterile powders in ampoule A is dissolved with a portion (5–10 ml) of diluent from vial B; the mixture is then transferred, under sterile conditions, to vial B, corrected to about pH 7.5 with sterile phosphate buffer if necessary, and injected by slow intravenous infusion over 1 hour.

EXAMPLE 4

| | |
|---|---|
| Ampoule A - Active ingredient (see Example 2) | |
| Vial B - Diluent | |
| Soybean lipids | 50 g |
| Egg yolk phospholipids | 6 g |
| Glycerol | 11.25 g |
| Bidistilled water for injections, q.s. ad | 500 ml |

The same procedure as in example 3 is followed and, finally, the resulting mixture is injected by slow intravenous infusion over 3 hours.

EXAMPLE 5

| | |
|---|---|
| Ampoule A - Active ingredient (see Example 2) | |
| Ampoule B - Diluent | |
| Egg yolk phospholipids | 50 mg |
| Glucose | 500 mg |
| Benzyl alcohol | 50 mg |
| Bidistilled water for injections q.s ad | 10 ml |

The mixture of sterile powders in ampoule A is dissolved with the diluent from ampoule B at the time of use and the resulting mixture is slowly injected as a bolus dose, by intravenous route.

EXAMPLE 6

| | |
|---|---|
| Ampoule A - Active ingredient | |
| SPA-S-843 | 50 mg |
| Lactose | 50 mg |
| Mannitol | 100 mg |
| Vial B - Diluent | |
| Egg yolk phospholipids | 75 mg |
| Glucose | 12.5 mg |
| Glycerol | 5.6 g |
| Distilled water for injections, q.s. ad | 500 ml |

Before use, the content of ampoule A is dissolved with the diluent from vial B and the resulting mixture injected by slow intravenous infusion.

EXAMPLE 7

| | |
|---|---|
| Ampoule A - Active ingredient | |
| SPA-S-843 | 25 mg |
| Deoxycholate sodium | 20 mg |
| 0.1N sodium hydroxide q.s. ad pH | 8.5/9 |
| Bidistilled water for injections, q.s. ad | 5 ml |
| Vial B - Diluent | |
| Soybean lipids | 10 g |
| Egg yolk phospholipids | 1.2 g |
| Glycerol | 2.25 g |
| Benzyl alcohol | 0.5 g |

The opalescent solution in ampoule A, containing the active ingredient as a free base, is added to the diluent in vial B and the resulting mixture injected by slow intravenous infusion.

EXAMPLE 8

| | |
|---|---|
| Ampoule A - Active ingredient (see Example 2) | |
| Vial B - Diluent | |
| Triolein | 10 g |
| Soybean phospholipids (soybean lecithin) | 1 g |
| Xylitol | 3 g |
| Bidistilled water for injection q.s ad | 100 ml |

The content of ampoule A is treated with the diluent from vial B and administered by slow intravenous infusion, as indicated in Example 3.

EXAMPLE 9

| | |
|---|---|
| Ampoule A - Active ingredient | |
| SPA-A-843 | 50 mg |
| Sodium deoxycholate | 40 mg |
| Vial B - Diluent | |
| Soybean lipids (soybean oil) | 10 g |
| Soybean phospholipids | 1.2 g |

-continued

| Ampoule A - Active ingredient | |
| --- | --- |
| (soybean lecithin) | |
| Glycerol | 2.25 g |
| Bidistilled water for injection q.s. ad | 100 ml |

The active ingredient in ampoule A is treated with the diluent from vial B and administered as described in example 3.

EXAMPLE 10

| Ampoule A - Active ingredient | |
| --- | --- |
| SPA-S-843 | 10 mg |
| Vial B - Diluent | |
| Distearoylphosphatidylcholine | 25 mg |
| Glucose | 12.5 g |
| Deoxycholate sodium | 10 mg |
| Benzyl alcohol | 1.25 g |
| Distilled water for injection q.s. ad | 250 ml |

The content of ampoule A is dissolved with the diluent from vial B and the resulting mixture injected by slow intravenous infusion.

EXAMPLE 11

| | |
| --- | --- |
| SPA-S-843 | 50 mg |
| Ascorbic acid | 9.0 mg |
| Lactose | 250 mg |
| Soybean lipids | 1000 mg |
| Egg yolk phospholipids | 120 mg |
| Glycerol | 225 mg |
| Bidistilled water for injection q.s. ad | 10 ml |

The mixture, pH 5.5, is slowly injected by intravenous route as a bolus dose.

EXAMPLE 12

An injectable preparation of active ingredient (ampoule A—50 mg of SPA-S-843) in 100 ml of a lipid emulsion (vial B) having the composition reported in Example 3 and obtained with the procedure as in the same Example 3, was compared for local tolerance with a formulation obtained by dissolving the content of another ampoule A, same as before, in 100 ml of 5% glucose standard solution. Both formulations (lipid and glucose) contained 0.5 mg of SPA-S-843/ml.

The tests were carried out in five adult male New Zealand albino rabbits weighing 2.8±0.2 kg, by daily injecting intravenously, over a time of 120 seconds, 2 ml in total (1 mg of SPA-S-843) of both lipid and glucose solutions into the marginal veins of the left and right ear respectively. This treatment was repeated for 3 or more days.

At 24 hours following each injection, and before performing the next injection, the sites were checked for local damage brought about by administration of the drug. Damage was rated according to the following arbitrary point rating scale: 0=no damage; 1=mild inflammation; 2=hyperaemia/inflammation; 3=inflammation/necro-sis (0–2 mm); 4=necrosis (3–5 mm).

| Rabbit no. | Lipid formulation (left ear) | | Formulation in glucose (right ear) | |
| --- | --- | --- | --- | --- |
| | 1 injection | 3 injections | 1 injection | 3 injections |
| 1 | 0 | 1 | 1 | 3 |
| 2 | 1 | 1 | 3 | 4 |
| 3 | 0 | 1 | 2 | 4 |
| 4 | 0 | 0 | 1 | 3 |
| 5 | 1 | 1 | 2 | 4 |

A great difference was seen between the effects on the left and on the right ears of the two treatments. The left ear, treated with the lipid formulation, had remained substantially free from damage, showing only mild inflammation at the site of injection, substantially due to the mechanical action of the needle. The right ear, treated with the glucose formulation, was found mildly hyperemic in some animals, as of the 1st injection. Local damage was growing progressively worse throughout observation, showing presence of widespread thrombotic formation and evident signs of necrosis after 3 days, making it impossible to continue treatment.

Notwithstanding the special sensitivity of the experimental model in the rabbit, the relatively high concentration of the test drug and the speed of administration, the partricin derivative lipid formulation was found definitely better than the formulation in glucose solution and its tolerance by the vasal endothelium good.

EXAMPLE 13

The same lipid formulation as described in Example 12 was tested in the same experimental model by protracting the number of administrations into the rabbit ear marginal vein. Even after 20 injections local damage was modest and substantially identical to that observed after 1–3 administrations.

EXAMPLE 14

By proceeding as in Example 12, but performing the injections into the central artery of the rabbit ear, the SPA-S-843 lipid formulation substantially confirmed the substantial absence of local reactions and the superiority in comparison with standard injectable formulations.

EXAMPLE 15

SPA-S-843 free base was dissolved under nitrogen in a mixture of methylene chloride:methanol in the ratio 9:1 (1 mg/ml) and mixed with an equal volume of a methylene chloride solution of phospholipids (hydrogenated phosphatidylcholine and distearoyl phosphatidyl-choline) and with a methanol:methylene chloride solution of cholesterol, so as to give a molar ratio of drug to lipids of 1:5:2:2.5, and the solvents were removed under reduced pressure. In other tests, the phospholipids were represented, for instance, by egg lecithin alone.

The dried drug-phospholipid film was suspended in a standard phosphate-saline buffer (PSB) and hand-shaken allowing the film to form lipidic vescicles. The suspension was centrifuged for 1 hour and the pellet was additioned with maltose in the ratio 1:1 (w/w) and lyophilized. Following reconstitution with water for injection, in the proportion of 1 mg of active ingredient/ml, the resulting mixture is injected by slow intravenous infusion over 1 hour.

In single dose testing in mice, the i.v. 50% lethal dose ($LD_{50}$) of the SPA-S-843 formulation, obtained according to Example 15, is increased from 70 mg/kg to >200 mg/kg

EXAMPLE 16

A mixture of 25 mg of SPA-S-843, f.i. in the form of free base, 2.5 g of soybean oil and 2.5 g of egg-lecithin is treated with water under stirring to give an emulsion, the mixture is added with 5 g of maltose while stirring and preserved as a lyophilized formulation.

After reconstitution with sterile distilled water, just before the use, the active ingredient is present as lipid nanosphere—encapsulated particles, having an average size of 25 to 50 nm. The mixture is then diluted with 5% dextrose to the desired concentration, usually to 100 ml, to be injected by slow infusion within 1 hour by i.v. route. The formulation shows a good distribution to sites of infection and low uptake by reticuloendothelial system.

What is claimed is:

1. A pharmaceutical formulation, comprising:

at least one derivative of partricin in the form of a free base or a pharmaceutically acceptable water-soluble salt thereof with at least one pharmaceutically acceptable acid or at least one pharmacologically acceptable acid;

a solubilizing/dispersing medium comprising at least one emulsion selected from the group consisting of a lipid emulsion in water and a phospholipid emulsion in water, wherein the resulting emulsion is iso-osmotic and the resulting formulation is intravenously injectable.

2. A formulation according to claim 1, comprising a partricin derivative in the form of a free base, a surface active agent and/or a co-solvent.

3. A formulation according to claim 1, comprising a pharmaceutically acceptable salt of the partricin derivative with at least one acid equivalent.

4. A formulation according to any preceding claim 1, comprising a pharmaceutically effective quantity of the partricin derivative.

5. A formulation according to any preceding claim 1, wherein the partricin derivative is a derivative of partricin A and/or B.

6. A formulation according to any preceding claim 1, wherein the partricin derivative presents the carboxyl in position C18 of the macrolidic ring in the form of ester or of neutral amide or of amide containing, in the side chain, a basic nitrogen group.

7. A formulation according to claim 6, wherein the partricin derivative is substituted on the primary amino group of mycosamine in the form of amide, with an acid containing a basic nitrogen group in the side chain.

8. A formulation according to any preceding claim 1, wherein the partricin derivative is N-dimethylaminoacetyl-partricin A 2-dimethylamino-ethylamide diascorbate, as such or as its free base.

9. A formulation according to claim 1, wherein the partricin derivative quantity is comprised between 1 and 100 mg.

10. A formulation according to claim 1, wherein the partricin derivative is in solution, micellar pseudosolution, as encapsulated inclusion compound, or submicronized particle suspensions, wherein the particle size is less than 5 $\mu$m.

11. A formulation according to claim 1, wherein the lipid and/or phospholipid emulsion is in the form of an oil-in-water emulsion, made up of droplets, vesicles, nanospheres, and wherein the lipids and/or phospholipids are of animal and/or vegetable and/or synthetic and/or semisynthetic origin.

12. A formulation according to claim 1, wherein the emulsion contains lipids selected from the group of the mono-, di- or triglycerides.

13. A formulation according to claim 12, wherein the lipids are triglycerides of vegetable origin.

14. A formulation according to claim 12, wherein the lipids are of animal origin.

15. A formulation according to claim 1, wherein the emulsion contains phospholipids of vegetable origin.

16. A formulation according to claim 1, wherein the emulsion contains phospholipids of animal origin.

17. A formulation according to claim 1, comprising phospholipids selected from the group consisting of distearoylphosphatidylcholine, dimyristoylphosphatidylcholine, dirimistoylphosphatidylglycerol, phosphatidylethanolamine, phosphatidylserine, and phosphatidylinositol.

18. A formulation according to claim 1, comprising hydrogenated lipids and/or phospholipids.

19. A formulation according to claim 1, wherein the quantity of lipids is comprised between 1 and 25%.

20. A formulation according to claim 1, wherein the quantity of phospholipids is comprised between 0.5% and 5%.

21. A formulation according to claim 1, comprising a pharmaceutically acceptable excipient and/or adjuvant.

22. A formulation according to claim 21, wherein the excipient and/or adjuvant is at least one member selected from the group consisting of a sugar, antioxidant, preservative, ionic surfactant, non-ionic surfactant, acidic buffer, neutral buffer, basic buffer, co-solvent, stabilizer, polyalcohol, and sterol.

23. A procedure for the preparation of the formulation according to claim 1, comprising sterilizing a solution, micellar pseudo-solution or suspension of sub-micronized particles of the partricin derivative, and subsequently mixing with the emulsion.

24. A procedure according to claim 23, comprising drying, subsequent to sterilization, of the solution, pseudo-solution or suspension of the partricin derivative and subsequently mixing with the emulsion.

25. A procedure according to claim 23, wherein the partricin derivative is a free base, comprising adding a surfactant, co-solvent, or mixtures thereof to the partricin derivative, or sonicating the particles, or elevating the temperature of the solution, micellar pseudo-solution or suspension from room temperature to a temperature of from 40° C. to 50° C., and subsequently mixing with the emulsion.

26. A pharmaceutical form comprising a formulation according to claim 1, wherein the partricin derivative is enclosed in the lipid and/or phospholipid emulsion optionally together with the excipient and/or adjuvant.

27. A pharmaceutical form comprising a formulation according to claim 1, wherein the partricin derivative is preserved in the anhydrous state optionally together with the excipient and/or adjuvant, separated from the lipid and/or phospholipid emulsion, optionally together with the excipient and/or adjuvant.

28. A method for the treatment of pathologies sensitive to the action of a partricin derivative, comprising administering the intravenously injectable pharmaceutical formulation according to claim 1 to an animal in need of such treatment.

29. The formulation according to claim 3, which comprises two acid equivalents of said pharmaceutically acceptable salt of the partricin derivative.

30. The formulation according to claim 9, wherein said partricin derivative quantity is from 10 to 50 mg.

31. The formulation according to claim 10, wherein said particle size is less than or equal to 3 μm.

32. The formulation according to claim 13, wherein said triglycerides of vegetable origin are soybean or olive triglycerides.

33. The formulation according to claim 14, wherein said lipids are fish oils.

34. The formulation according to claim 15, wherein said phospholipid is phosphatidylcholine.

35. The formulation according to claim 15, wherein said phospholipid is soybean lecithin.

36. The formulation of claim 16, wherein said phospholipid is phosphatidylcholine.

37. The formulation of claim 16, wherein said phospholipid is egg yolk lecithin.

38. The formulation of claim 19, wherein the quantity of lipids is from 10 and 20%.

39. The pharmaceutical of claim 27, wherein said anhydrous state is in the form of a lyophile.

40. The pharmaceutical formulation of claim 1, wherein the partricin derivative is a derivative of partricin A or partricin B.

41. The pharmaceutical formulation of claim 40, wherein the partricin derivative is a derivative of partricin A or partricin B having a carboxyl at position C18 of the macrolidic ring.

42. The pharmaceutical formulation of claim 41, wherein the carboxyl is selected from the group consisting of an ester, neutral amide, and amide containing a basic nitrogen group in the side chain.

43. The pharmaceutical formulation of claim 40, wherein the derivative of partricin A or partricin B is further substituted with an acid containing a basic nitrogen group in the side chain, wherein the acid is on the primary amino group of mycosamine.

* * * * *